US 12,123,864 B2

(12) United States Patent
Stenstrom et al.

(10) Patent No.: US 12,123,864 B2
(45) Date of Patent: Oct. 22, 2024

(54) HIGH TEMPERATURE HIGH PRESSURE ASPHALTENE DEPOSITION/INHIBITOR SCREENING TEST

(71) Applicant: Schlumberger Technology Corporation, Sugar Land, TX (US)

(72) Inventors: Tyler Stenstrom, Houston, TX (US); Farshid Mostowfi, Lexington, MA (US); Christopher Harrison, Auburndale, MA (US); Graham Drummond, Aberdeen (GB); Matthew Sullivan, Westwood, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/698,885

(22) PCT Filed: Oct. 5, 2022

(86) PCT No.: PCT/US2022/045734
§ 371 (c)(1),
(2) Date: Apr. 5, 2024

(87) PCT Pub. No.: WO2023/059684
PCT Pub. Date: Apr. 13, 2023

(65) Prior Publication Data
US 2024/0319162 A1 Sep. 26, 2024

Related U.S. Application Data

(60) Provisional application No. 63/262,097, filed on Oct. 5, 2021.

(51) Int. Cl.
| | | |
|---|---|---|
| G01N 33/28 | (2006.01) |
| G01N 21/25 | (2006.01) |
| G01N 30/20 | (2006.01) |
| G01N 30/34 | (2006.01) |

(52) U.S. Cl.
CPC ......... G01N 33/2835 (2013.01); G01N 21/25 (2013.01); G01N 30/20 (2013.01); G01N 30/34 (2013.01); G01N 33/2823 (2013.01)

(58) Field of Classification Search
None
See application file for complete search history.

(56) References Cited

U.S. PATENT DOCUMENTS

| 7,523,648 B2 | 4/2009 | Zougari |
| 10,436,691 B2 | 10/2019 | Fouchard |
| 2012/0158315 A1 | 6/2012 | Trygstad |

(Continued)

OTHER PUBLICATIONS

International Search Report and Written Opinion issued in International Patent application PCT/US2022/045734 on Jan. 31, 2024, 9 pages.

(Continued)

*Primary Examiner* — Xiaoyun R Xu
(74) *Attorney, Agent, or Firm* — Jeffrey D. Frantz

(57) ABSTRACT

Embodiments presented provide for a method and apparatus for testing a sample fluid for asphaltene deposition. The apparatus provides two testing cylinders and a transfer pump to transfer fluid from the first cylinder to the second cylinder and back again while pressure is varied on the testing fluid, while a spectrometer evaluates the fluid during the pressure variation.

10 Claims, 16 Drawing Sheets

(56) References Cited

U.S. PATENT DOCUMENTS

2016/0258875 A1 9/2016 Pearl
2017/0115266 A1 4/2017 Ratulowski
2020/0256189 A1 8/2020 Sullivan

OTHER PUBLICATIONS

Madhi, et al., Screening of inhibitors for remediation of asphaltene deposits: Experimental and modeling study, Petroleum, Jun. 2018, vol. 4, Issue 2, pp. 168-177.
Juyal et al., "Joint Industrial Case Study for Asphaltene Deposition" Energy Fuels 2013, 27(4): 1899-1908.
Kharrat et al., "Asphaltene Content Measurement Using an Optical Spectroscopy Technique" Energy Fuels 2013, 27(5): 2452-2457.
Ghloum et al,. "Mitigation of asphaltenes precipitation phenomenon via chemical inhibitors." Journal of Petroleum Science and Engineering, 2019, 175: 495-507.
"Asphwax Testing Services." Retrieved Feb. 26, 2021, from http://www.asphwax.com/laboratory.html.
Schlumberger (2021). "Reservoir Laboratories Testing Brochure." Retrieved Feb. 26, 2021, from https://www.slb.com/-/media/files/testing-services/brochure/reservoir-laboratories-br.ashx.
Jennings et al. Asphaltene Inhibitor Testing: Comparison Between a High Pressure Live-Fluid Deposition and Ambient Pressure Dead-Oil Asphaltene Stability Method. Offshore Technology Conference, 2018, 15 pages.
PSL Systemtechnik, G. "Differential Dynamic Scale Loop" Retrieved Feb. 26, 2021, from https://www.pslsystemtechnik.com/en/differential-scale-loop, 4 pages.
Gon et al., "Modified Asphaltene Capillary Deposition Unit: A Novel Approach to Inhibitor Screening" Energy Fuels, 2016, 30(5): 3687-3692.
Salimi et al., (2016) "Investigation of asphaltene deposition under dynamic flow conditions" Petroleum Science 13(2): 340-346.
Kuang et al. (2018). "Investigation of Asphaltene Deposition at High Temperature and under Dynamic Conditions" Energy Fuels 32(12): 12405-12415.
Takabayashi et al., (2020). Practical Prediction of Asphaltene Mitigation Based on Dynamic Asphaltene Inhibitor Test DAIT. SPE Asia Pacific Oil Gas Conference and Exhibition, 17 pages.
Ghloum et al., (2004). "Investigation of Asphaltene Precipitation Process for Kuwaiti Reservoir" Petroleum Science and Technology vol. 22 Nos. 7 8: 1097-1117.
Vilas Boas Favero et al., (2016). "Mechanistic Investigation of Asphaltene Deposition." Energy Fuels 30(11): 8915-8921.
International Preliminary Report on Patentability issued in International Patent application PCT/US2022/045734, dated Apr. 18, 2024, 7 pages.

HIGH TEMPERATURE HIGH PRESSURE ASPHALTENE DEPOSITION/INHIBITOR SCREENING TEST

CROSS-REFERENCE TO RELATED APPLICATIONS

The present application is a National Stage Entry of International Application No. PCT/US2022/045734, filed Oct. 5, 2022, which claims priority to U.S. Provisional Application 63/262,097 dated Oct. 5, 2021, the entirety of which is incorporated by reference.

FIELD OF THE DISCLOSURE

Aspects of the disclosure relate to testing of downhole fluids. More specifically, aspects of the disclosure relate to high temperature and high pressure asphaltene deposition tests for the hydrocarbon recovery industry.

BACKGROUND

Asphaltenes are one of the most problematic flow assurance issues one can encounter in the production of oil and gas. Under reservoir conditions, asphaltene compounds are typically fully soluble in the pressurized (live) oil. However, as production begins, the live oil is subjected to reductions in pressure and temperature as well as blending with other fluids as the live oil flows from the porous media environment of the reservoir, into the well-bore, through production tubulars, flow lines, chokes, valves, pumps and other production equipment. The changes in pressure, temperature, and composition of the live oil during production may lead to the precipitation (i.e. formation of a second liquid or solid phase) and possibly deposition (i.e. adherence of the precipitate to a solid surface). Oils demonstrating this type of asphaltene precipitation and deposition behavior are typically referred to as unstable. Destabilized oils that are present during production can potentially, under the appropriate flow conditions, begin to adhere and build up on any surface. This leads to restrictions in the inner diameter of the tubing, restricting flow and fouling production equipment. Changes to the inner diameter of tubing can cause significant changes in production rates as well as potentially leading to blockages in equipment containing narrow flow passages.

Once formed, the asphaltene build ups (or deposits) can become difficult to remove. Land intervention for such deposits are estimated to cost upwards of $0.5 MM USD and offshore wield a much higher price tag of $3.0 MM USD; these blockages also carry with them a loss of daily production revenue of up to $1.2 MM per day (cost estimates at 40 MBPD and ~$30/BBL oil)[1]. Due to the large amount of time/money that can be lost at the hands of accumulation of unwanted asphaltenes, there are many parties interested in preventing the build-up of these problematic compounds in production equipment and reservoirs; indeed, the research behind asphaltene deposition is large and ever-growing.

A large industry has surfaced around treating and preventing asphaltene deposits in the piping and equipment associated with production. One of the most widely used methods of treatment is to introduce small doses of chemical inhibitors (100-1000 ppm) that modify the composition of the oil within the production lines. The performance of asphaltene inhibitors, however, is oil specific. An inhibitor that works well on one type of oil may not work well on others or may even cause problems to worsen in other oils. It is, therefore, important and highly valuable to properly select treatment specific to each oil and to be able to screen the efficacy of these inhibitors conclusively.

There is a need to provide an apparatus and methods that easier to operate than conventional apparatus and methods and allow for high temperature and high pressure evaluation of asphaltene deposition.

There is a further need to provide apparatus and methods that do not have the difficulties discussed above.

There is a still further need to reduce economic costs associated with operations and apparatus described above with conventional tools and to allow for efficient evaluation of asphaltene deposition.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one example embodiment, a method of determining asphaltene deposition values for a sample of oil, is disclosed. The method may comprise adding an inhibitor to a precision injection tube and bringing an asphaltene sampling system to a specified temperature and pressure. The method may also comprise calibrating a spectrometer when the asphaltene system is in a vacuum state and placing the sample of oil into the asphaltene sampling system. The method may also comprise opening an injection valve in an injection line and filling the injection line of the asphaltene sampling system up to a first cylinder valve and second cylinder valve with the inhibitor and the sample. The method may also comprise opening the first cylinder valve for the first cylinder to fill the first cylinder with a portion of the sample of oil at a desired cylinder flow rate and monitoring the first cylinder to determine a filled condition. The method may also comprise closing the injection valve upon a determination of the filled condition of the first cylinder and opening a second cylinder valve for the second cylinder. The method may also comprise transferring a portion of the sample fluid to transfer into the second cylinder from the first cylinder and closing the second cylinder valve and establishing a pump flow for a first cylinder pump. The method may also comprise closing the injection valve and opening the second cylinder valve, establishing a transfer flow between the first cylinder and the second cylinder of a portion of the sample fluid and dropping a pressure in the system at a desired pressure decrease. The method may also comprise testing at least one of a deposition test and an optical density evaluation of the sample during the dropping of the pressure in the system to determine an asphaltene onset pressure.

In another example embodiment, a system for testing for asphaltene deposition is disclosed. The system may comprise a precision injection tube, an injection valve and an injection line, the injection valve connected to the injection line a first cylinder valve and a second cylinder valve connected to the injection line and a first testing cylinder connected to the first cylinder valve. The system may also comprise a second testing cylinder connected to the second cylinder valve, at least one pump configured to transfer fluid from the first testing cylinder to the second testing cylinder and a spectrometer connected to at least one of the first testing cylinder and the second testing cylinder.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not be considered limiting of its scope, for the disclosure may admit to other equally effective embodiments.

Figure 1:
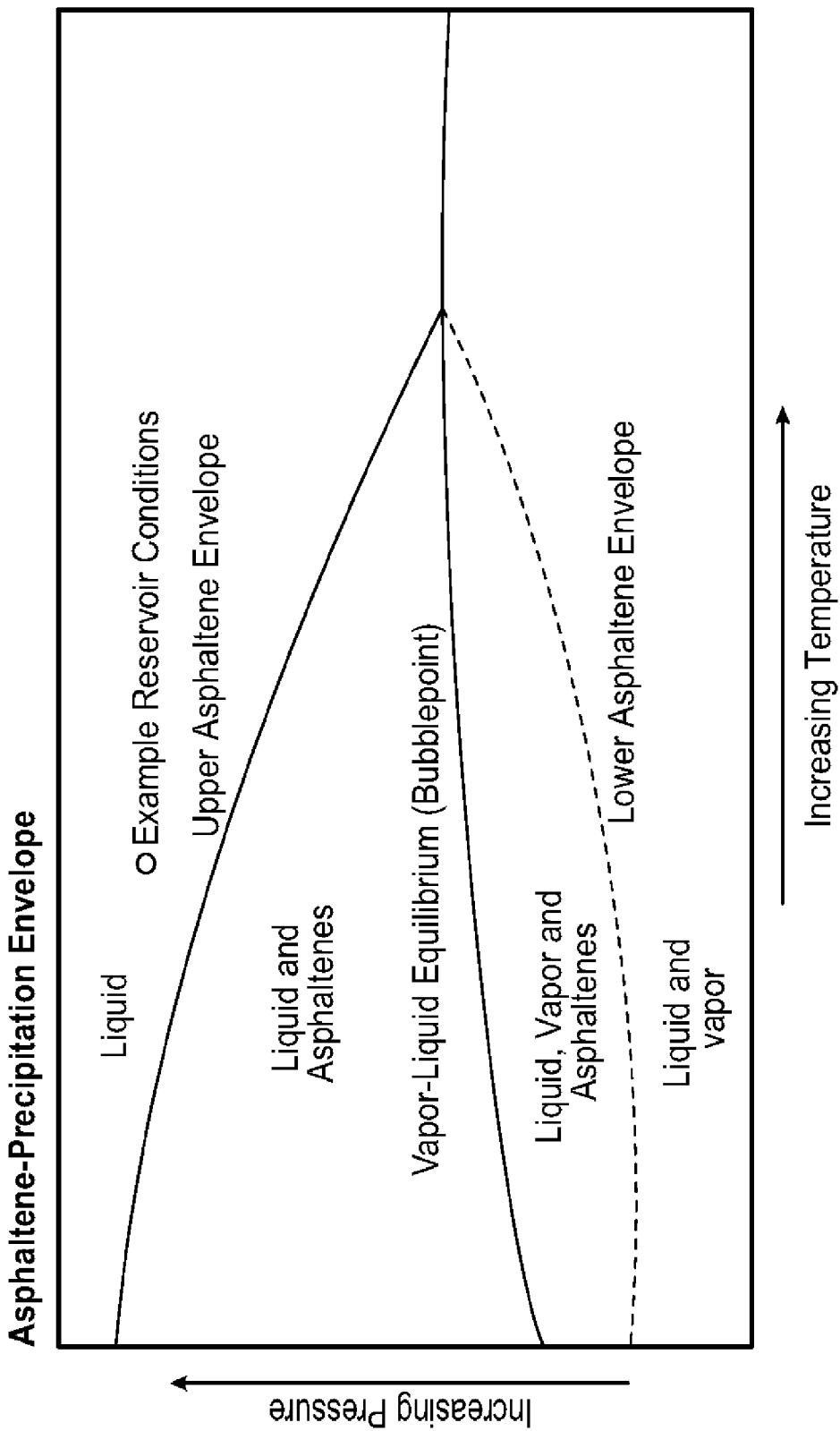
FIG. 1 is a example asphaltene phase diagram.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, components, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Asphaltene deposition and inhibitor testing are common research topics. There are many methods that have been attempted to study asphaltene deposition and the performance of inhibitors to prevent deposition, but all had issues with reliability, feasibility, or even lacked a likelihood that they could be reasonably compared to deposition as it occurs in the field. This is especially true when it comes to more realistic temperature and pressure conditions. Creating a test that will reliably yield a deposit to screen asphaltene inhibitors under high temperature high pressure, hereinafter "HTHP" conditions is not an easily obtainable objective for many chemical companies in the industry.

For deposition to occur, asphaltenes must become destabilized into nanoaggregates that can adhere to each other and surfaces they encounter. Changes to thermodynamic properties during production causes this destabilization. An example phase envelope for asphaltene stability is shown in FIG. 1. Precipitation during production takes place due to the presence of high concentrations of precipitants, the majority of which are gases at ambient condition and thus require pressurized liquid forms to interact with oils being studied. The higher pressure and temperature conditions in the reservoir keep the asphaltenes in solution until there is a sufficient reduction in pressure and temperature during the flow of oil up the production tubing to induce the precipitation of asphaltene and subsequently, the possibility leading to the occurrence of asphaltene deposition. The produced fluid undergoes a final phase separation at the surface separator creating a "dead oil" where the liquid oil phase is separated from the gaseous components that once comprised a single phase "live oil" within the reservoir.

When production chemistry companies test oils sent to them by oil producers, they are testing the dead oil liquid phase that comes after the phase separation. Due to this, there have been two main ways to precipitate asphaltenes to test for inhibitor effects. Asphaltenes can be forced out of solution using higher chain alkanes that are more stable at ambient conditions such as pentane, hexane and heptane. Indeed, heptane is the most commonly used precipitant for ambient studies. The preferred but more complicated approach is to take the dead oil and a synthetic multi-component gas and recombine them into an HTHP fluid that more closely resembles reservoir conditions. This is not a trivial process and is inaccessible by many chemical companies. Each alkane causes precipitation to occur at different rates and affects the classes of molecules that precipitate. Therefore, studying the effects of chemicals on only the heptane precipitated compounds neglects a potentially large range of molecules and their interactions from being studied and may lead to incorrect conclusions during screening. The method of precipitation will undoubtedly affect results of testing and opinions of customers.

Several commercial methods exist that allow observation of precipitation of asphaltenes. While they give an idea as to effects of chemicals on the nature of precipitation, they do not say anything about the ability of inhibitors to alter the "stickiness" of asphaltenes. These methods include high pressure microscopy and various solids detection systems (SDS) featuring narrow band light sources, such as lasers, and NIR spectroscopy.

In high pressure SDS, pressure is controlled using some form of PVT (pressure/volume/temperature) cell. A lab operator would collect the residual asphaltenes that deposit in the cell during depressurization and quantify them[7]. The reproducibility of this measurement has not been quantified but is understood to be relatively poor, with settling of asphaltenes contributing a significant but unknown amount to the observed deposit. As such, the data simply serves as additional information that accompanies the onset measurement performed with the SDS system. These tests generally consume a moderate amount of fluid (50 ml to 200 mL).

In other deposition studies, capillary tubing is employed as the primary deposition surface. Equipment such as the differential dynamic scale loop use pressure drops to identify arterial restrictions in tubing or filters due to formation of mineral deposits. Effective chemicals can be injected into the systems to determine reductions in or prevention of pressure drop which correlate to inhibition of scaling. Chemical compounds involved in scaling, in general, have a significantly higher affinity for the surfaces they deposit on relative to asphaltene molecule affinity and this allows for capillary tubing to be more feasible for scale study especially when it comes to flow rate and shear limitations.

In general, capillary tubing is ideal for a few different reasons:
  Lower volume consumption due to the use of smaller inner diameters
  Readily transitions to high pressure testing from ambient testing.
  Very easy to manipulate total surface area of a test system by simply changing the length of tubing sections Considering these facts, it is not surprising that capillary testing has been attempted for asphaltene deposition studies. In one such study, the authors showed lackluster results using both pressure reduction and mass measurements of deposition when using capillary tubing. Instead, the authors prefer an alternative method using coupons. Asphaltene deposition is extremely sensitive to shearing effects and most capillaries used have extremely small IDs (0.005-0.03"). Shear effects are inversely proportional to cross-sectional area, which means that smaller IDs cause exponentially higher shear rates even in very low flow rates. Experiments have confirmed that one can obtain reproducible deposits in capillary systems, but inhibitor performance can be masked due to the prevention of deposition beyond a limited shear-based maximum. Some commercial laboratories still use capillary testing with pressure drops in the face of documented failures because of its feasibility.

Another system for studying deposition is the packed bed. This was first employed in ambient conditions to study the kinetics of asphaltene deposition and has since been expanded to work at high pressure. Interestingly, the high-pressure method described in the paper does not use recombined fluids. They force precipitation with heptane and then pressurize the packed columns up to a maximum of 3,000 psi. Pressure, in this case, does not perform the expected role of controlling the solubility of the oil containing gas and, in turn, determining the solubility state of asphaltenes or the associated risk for deposition. Hence, it misses the reason for using higher pressures. In addition to this, while packed beds allow for increased surface area for deposits, they have complicated flow regimes. They come with many dead spaces which allow for accumulation of asphaltenes unrelated to deposition phenomena and cause filtration effects. This may be representative of pore spaces in the formation, but arterial blockage occurs in production tubing, and as such, packed beds are not representative flow environment for inhibitor screening tests.

The asphaltene rocker cell (ARC) is another method used to study high pressure asphaltene deposition. This method is a modified version of systems used to study gas hydrates. A high-pressure vessel contains a metal ball and magnetic sensors that detect movement of the ball as it rocks back and forth in a crude oil. A gas mixture is injected into the system and the asphaltenes precipitate. As the ball is slowly prevented from moving, it is assumed that the asphaltenes are causing a blockage in the system. This is an indirect measurement, and like the packed bed, is not representative of actual deposition environments we'd be interested in studying for inhibitor screening.

There is no industry standard for HTHP deposition of asphaltenes, but the closest to a standard would be Schlumberger's RealView technology. RealView is a flow device based on the Couette flow geometry, specifically circulating flow between two concentric cylinders where one is stationary and the other is rotating. The shear environment near the wall mimics that observed in pipeline/tubular flows and thus able to analyze deposition under turbulent flow, HPHT conditions. The Couette device allows for both batch testing and flow-through testing of live crude oil to collect deposits of asphaltenes with accurate flow and shear rates. The commercialized test is expensive and requires a significant amount of recombined/live sample to perform. Due to this, it is not commonly used for screening asphaltene inhibitors as that would require more throughput than many checkbooks would want to consider.

Many techniques have been used and even commercialized to study asphaltene inhibitor performance. Most of them are bootstrapping off techniques used to study other phenomena and do not engineer from first principles of asphaltene deposition as it relates to production tubing. In summary, there is a lot of room for improvement in terms of fluid use, flow regime and reliability when it comes to screening inhibitors which was the main purpose of the technology developed below.

EXAMPLES

As discussed earlier, deposition may occur due to asphaltenes precipitating during pressure and temperature changes as the live oil fluid traverses the production tubing or, at times, in the reservoir itself. Gas lift and other wellbore production technologies can alter the composition of the live oil fluid and destabilize problematic asphaltenes which can then restrict pipe flow or clog pore spaces. Reservoir fluids (i.e. live oils) can be naturally rich in asphaltene precipitants; these precipitants are generally gases in ambient conditions, but at higher pressures, are soluble in crude oils. Crude oils containing soluble gas under high pressure are often referred to as live oils. Higher temperatures and pressures make live oils a better solvent for these asphaltenes in the presence of these precipitants. However, reductions in pressure and temperature or the addition of more precipitants can destabilize the asphaltenes such that the asphaltenes will begin to precipitate as a separate liquid or solid, which can begin to grow into larger particles, flocculate into large clumps of particles, or deposit on solid surface, potentially causing damage to flow lines and process equipment. In order to best emulate downhole conditions in laboratory testing, a live oil sampled directly from a reservoir by an appropriate sampling device or a live oil recombined in a laboratory environment must be utilized. A recombined oil is synthesized by introducing a gas mixture into a dead oil and pressurizing the mixture in a temperature-controlled sample bottle. An apparatus capable of containing and manipulating this sample must be employed for testing.

Referring to FIG. 1: a basic schematic for test setup in conformance with one example embodiment of the disclosure is illustrated. The hydraulic and sample sides of the sample bottles/pistoned cylinders are shown in blue and brown, respectively. The pumps (not shown in the diagram) are connected to the hydraulic side (blue) of the bottle/pistoned cylinders.

Figure 2:
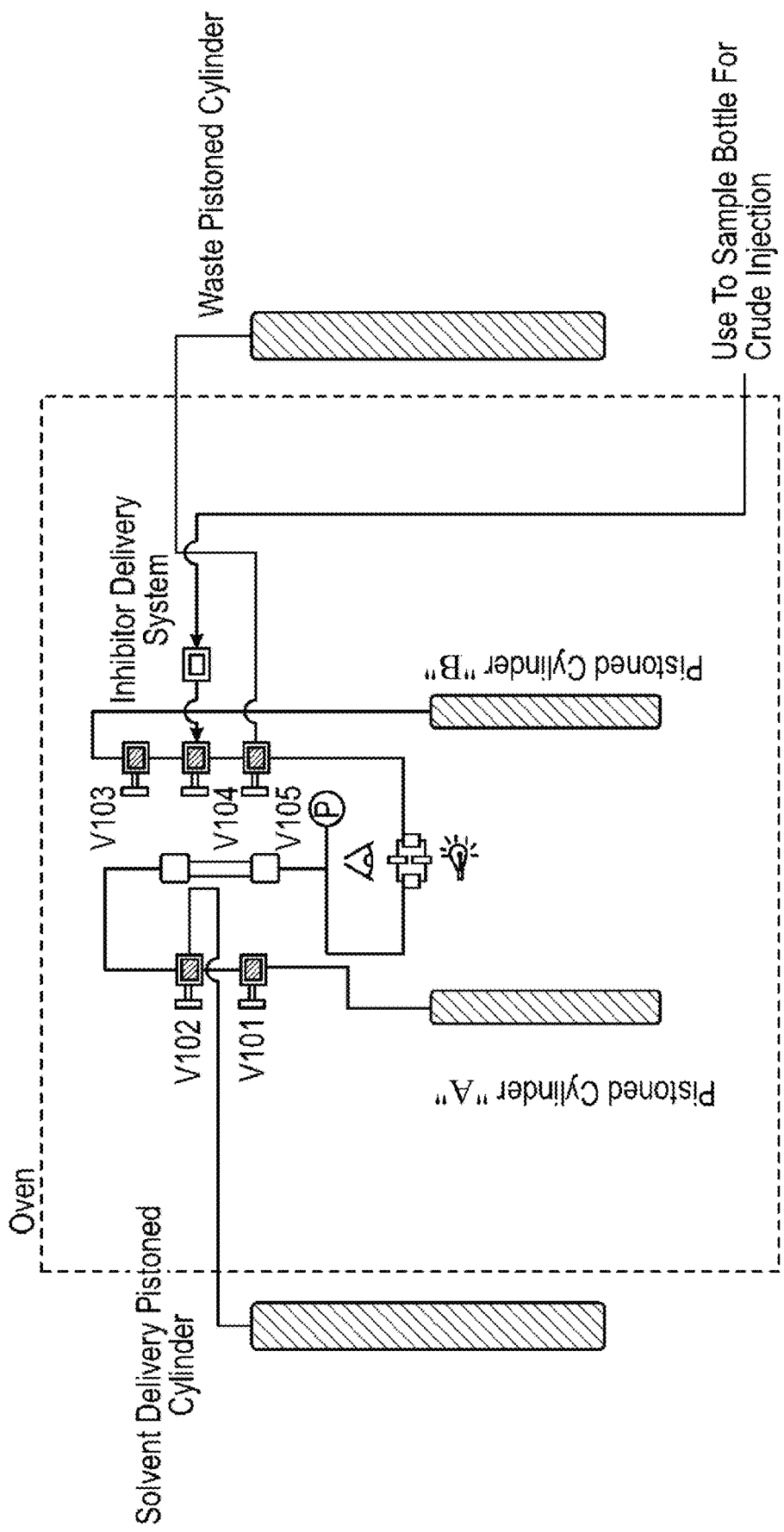
FIG. 2 is a schematic for a testing arrangement in one example embodiment of the disclosure.

The inhibitor screening apparatus and method being proposed describes a set-up to measure the amount of asphaltene deposit in a deposition tube that can occur during the depressurization of a live oil, the procedure to operate said apparatus and how the data is interpreted to determine if the presence of inhibitor has an effect on the measured amount of deposit. The inhibitor screening apparatus consists of many components (that can be of varying dimensions but the currently implemented dimensions will be discussed below) that have been situated in an oven to achieve appropriate fluid conditions. The main components of the system are listed and labeled in FIG. 2. Two pistoned-cylinders, "A" and "B", are separated into a sample and hydraulic side by a piston. High pressure syringe pumps are used to hydraulically manipulate the pressure of each pistoned-cylinders. The test fluid travels between the pistoned cylinder sample sides via the diagrammed flow lines. One of the main advantages of the current system is the volume. Current inner diameter/tubing dimensions reflect this volume focus and still allow pressures up to 20,000 psia and temperatures up to 250 degrees C. This is not a strict requirement, and larger components can be used to achieve higher pressure rating at the expense of volume of fluid used.

Figure 3:
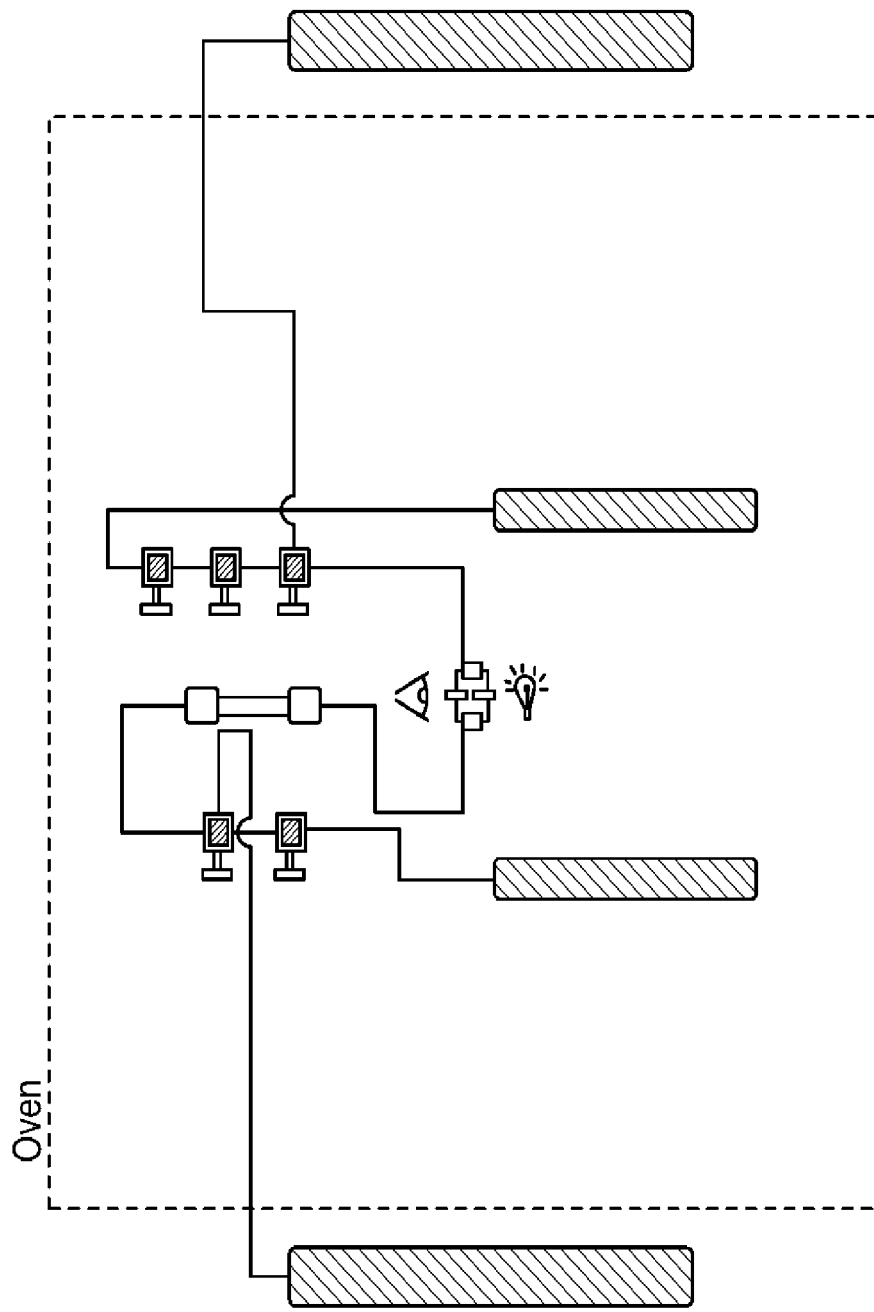
FIG. 3 is a diagram of a primary test flow path of the schematic of FIG. 2.
Figure 4:
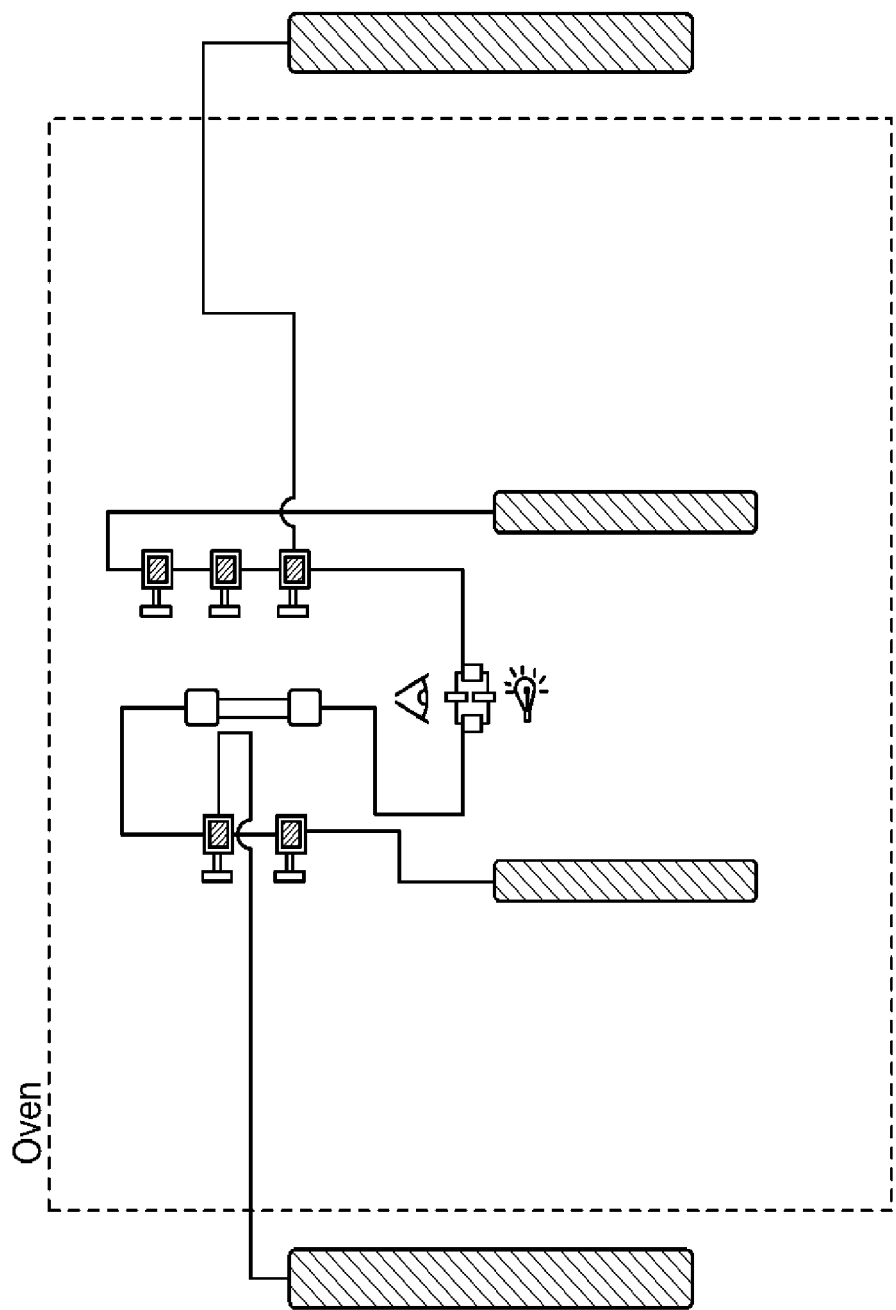
FIG. 4 is a solvent flushing path through the primary flow path to waste.
Figure 5:
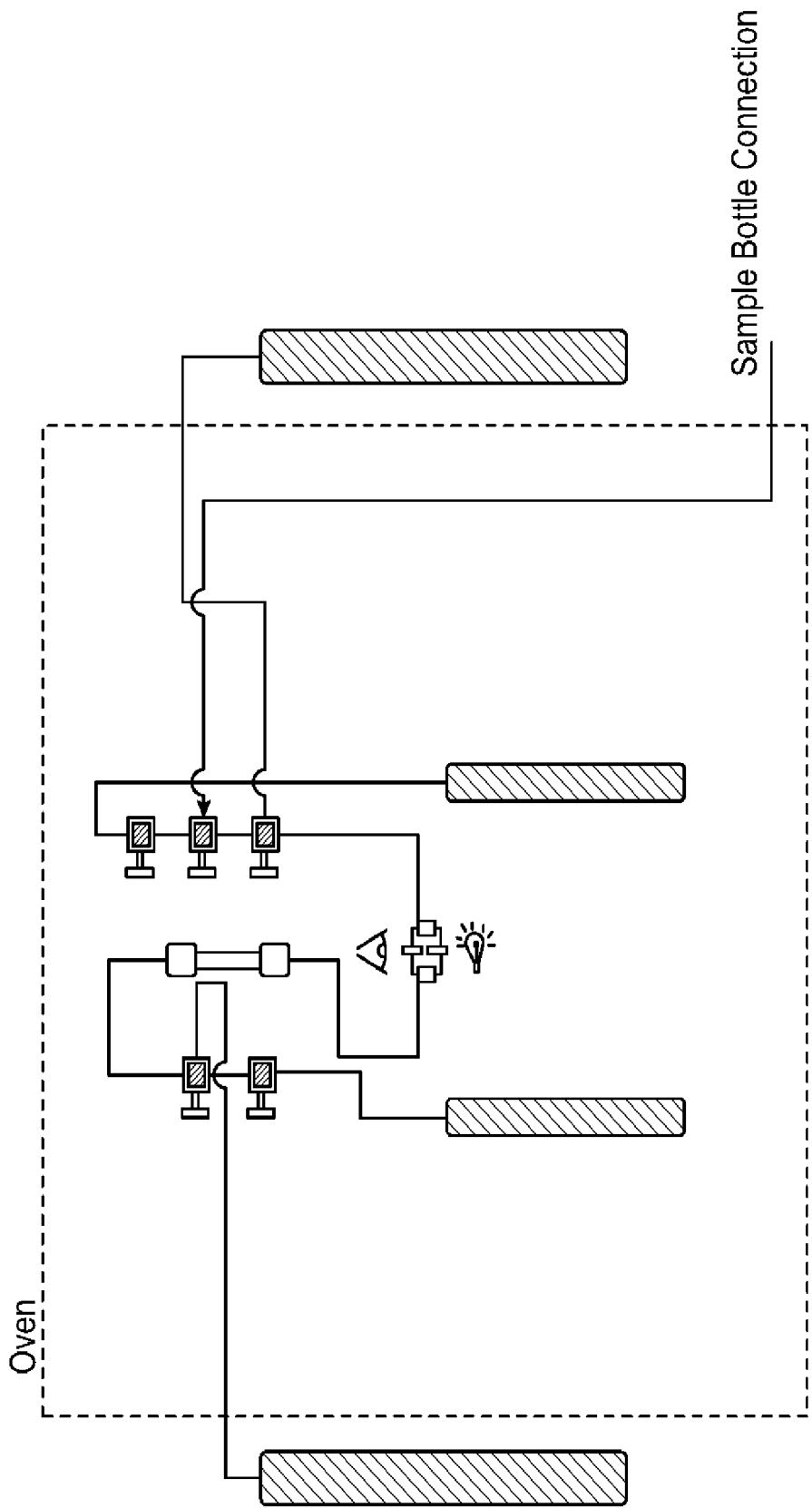
FIG. 5 is a crude injection flow path from a bulk sample.

Between pistoned cylinder A and B there are five valves and a system of tubing connected to the deposition tube, a pressure sensor, and a flow cell. Two of the valves are two-way isolation valves and they are connected directly to pistoned cylinders A and B; the remaining valves have two ports that are always open to flow and have a third port that can be open or closed leading outside the primary flow path. Within the setup, there are two distinct isolatable flow paths (FIGS. 3 and 4) where fluid can travel and one path that serves to inject sample into the system (FIG. 5); these flow paths are all connected to the primary flow system which includes the deposition tube, pressure sensor and flow cell. FIG. 3 shows the flow path used for testing a sample that has been injected into the system. The fluid will flow back and forth through the deposition tube between cylinders A and B. When the test is over, FIG. 4 shows the flow path used for displacing the crude from the system prior to depressurization.

Figure 6:
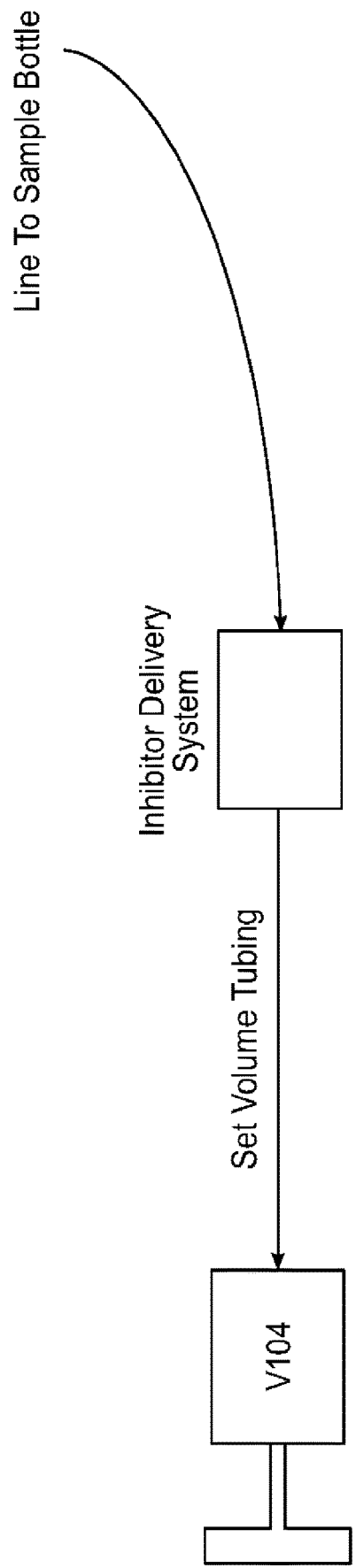
FIG. 6 is a sample injection schematic showing how fluid is transferred from a sample bottle into the testing apparatus.
Figure 7:
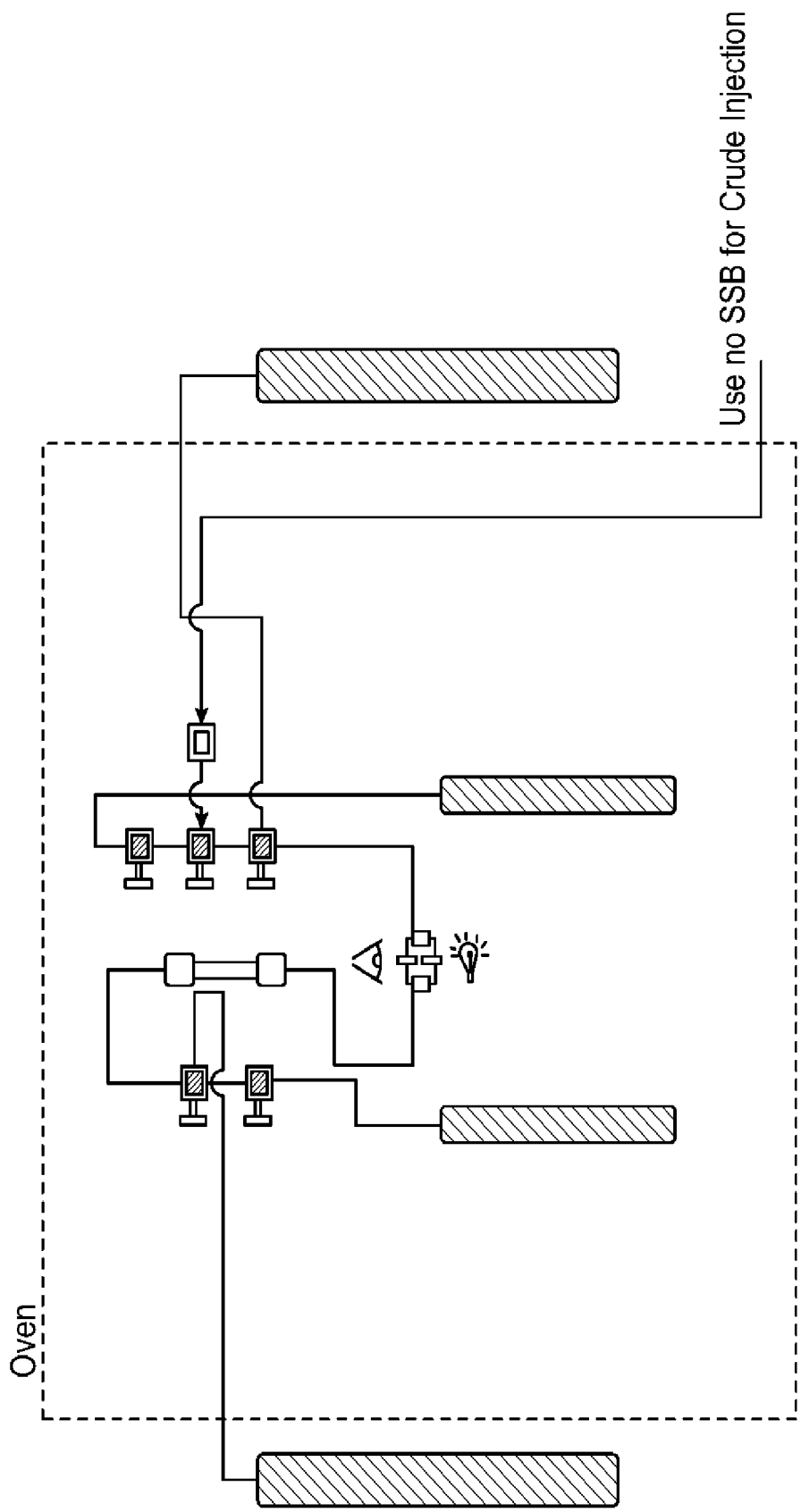
FIG. 7 is a diagram of a transfer of a sample from bulk storage.

In order to test inhibitors, a method for injecting chemicals into the neat fluid stream must be employed. A piece of tubing is cut to precise dimensions to hold the specific amount of chemical to be added. This piece of tubing is filled via syringe and then connected directly to the system in between the line from the sample bottle and the injection valve. This allows the inhibitor to be carried into the system when the test fluid is flashed into the testing apparatus. A diagram of this system is shown in FIG. 6.

Each test begins with a clean system. To clean the system, a solvent or solvent blend appropriate for removing any and all residual hydrocarbons in the apparatus may be used. In this specific embodiment, a solvent blend of 25 mL of a 90 wt % toluene/10 wt % methanol is pushed through the lines and followed with 10 ml of isopropanol. The isopropanol is then flushed from the system with nitrogen gas to evaporate remaining solvent in the lines while the oven preheats. The deposition tube is removed from the system during cleaning to be prepared separately and reduces the necessary volume for effective cleaning. The pistoned cylinders are disassembled between each test and thoroughly cleaned with the same toluene mixture and IPA, the pistons are given new seals and greased with a small amount of vacuum grease and then the pistoned cylinders are reassembled for the test.

Once the system is cleaned and all components are reattached and in place, the system can be prepared for sample injection. If an inhibitor is to be used, a precision injection tube is pre-filled with the chemical and connected to the injection port. The syringe containing the unused fluid remains connected to the back side of the tubing until it is ready to be connected to the sample bottle to prevent fluid from leaking out and changing the expected dose rate.

Before loading the sample into the system, the NIR spectrometer (900-2200 nm wavelength) is calibrated by taking dark/light references while the system is in a vacuum state after the oven has preheated. The two reference points (dark and light) determine the minimum and maximum amount of expected light. Once the sample is in the flow cell, the optical spectrum of the fluid can be processed using these two reference points. The optical spectrum of the fluid is collected continuously throughout testing.

Figure 8:
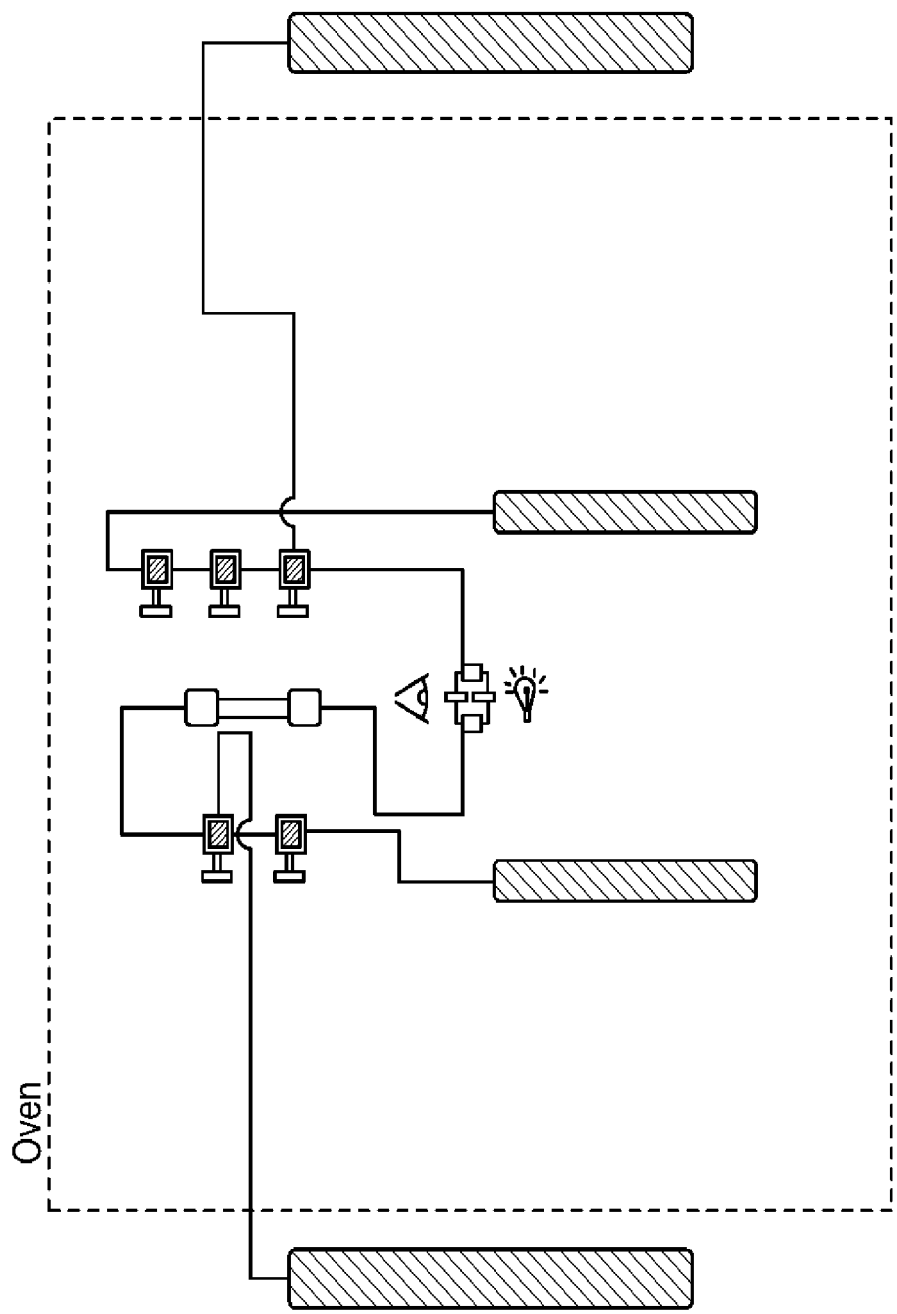
FIG. 8 is a diagram of an isolated system from bulk, filled with crude prior to mixing.

When all lines have been connected, the system maintains a vacuum, and the oven is at temperature, the fluid can be transferred into the system from the sample bottle. The necessary valves in the flow path are opened one at a time (valves 104 and 101) and the volume transferred from the bulk container is measured with each opening to ensure there is no leak in the system. First the valve of the bulk container is opened and fills the injection line (this valve is not pictured). Next, the injection valve (104) is opened, and the fluid fills the system up to both pistoned cylinder valves (101 and 103). Then, pistoned cylinder B's cylinder valve (103) is opened and pistoned cylinder B fills at 8 ml/min; the flowrate is controlled by the high pressure syringe pump connected to pistoned cylinder B's hydraulic side while the bulk storage fluid is kept at a constant pressure by its own high pressure syringe pump. Once pistoned cylinder B is full (FIG. 8), valve 104 is temporarily closed and pistoned cylinder A's cylinder valve (101) is opened. This allows some fluid to transfer into pistoned cylinder A and create more free volume in pistoned cylinder B. Valve 101 is closed again, pistoned cylinder B's pump is set to 1 ml/min and an additional milliliter of fluid is transferred into pistoned cylinder B. This additional fluid is necessary to obtain a specific pressure profile during the testing.

Figure 9:
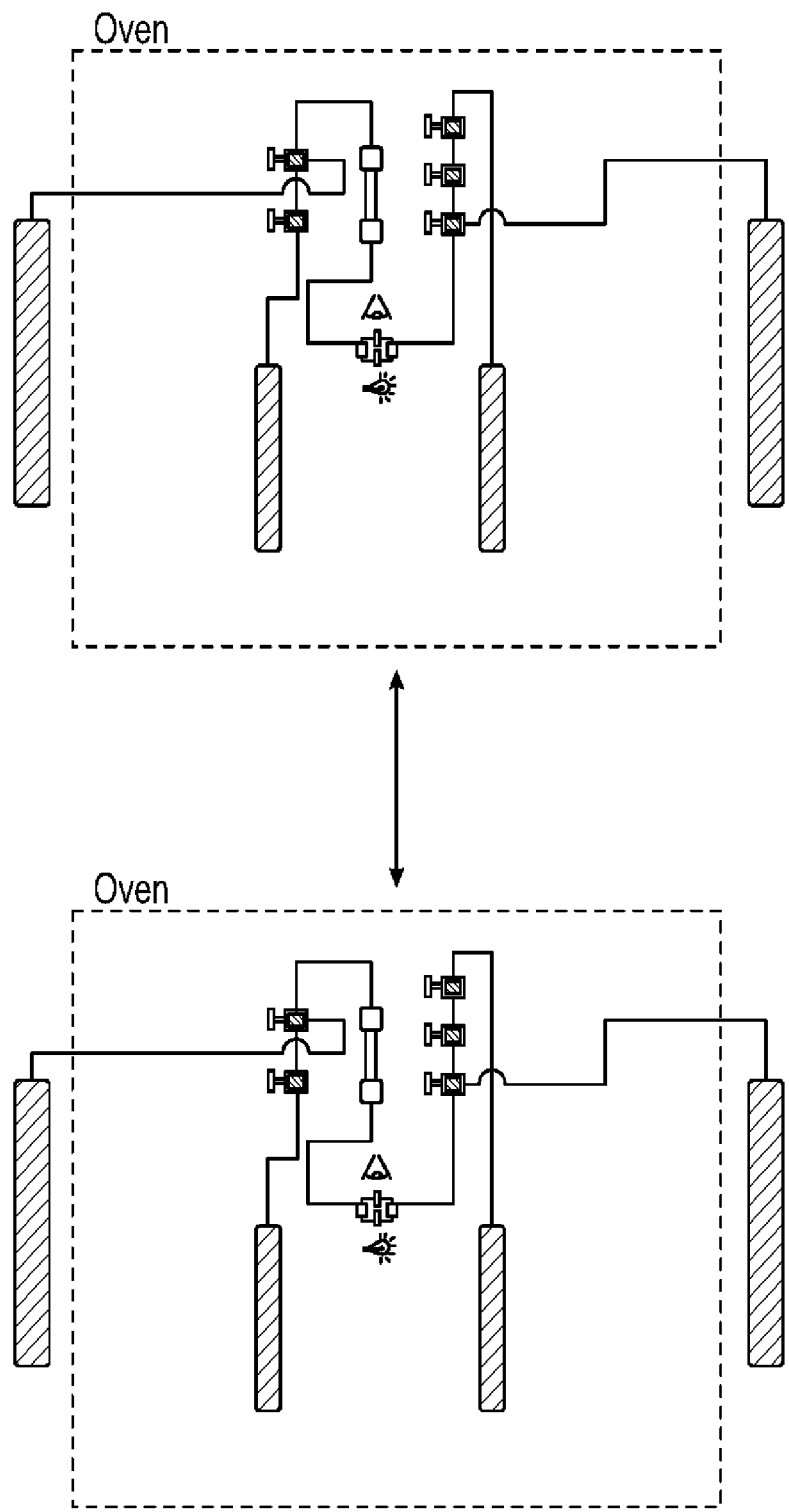
FIG. 9 is a mixing diagram showing the fluid being pushed back and forth between cylinder A and cylinder B.

Now that the fluid transfer is complete, injection valve 104 is closed and valve 101 is opened. Control of the pistoned cylinders is passed to a custom program on a connected computer to flow the sample back and forth between the two pistoned cylinders as in FIG. 9.

The flow rate is set between 1 and 30 ml/minute (typically 8 ml/min) and allowed to mix for 30 minutes. After thirty minutes have passed, the pressure is slowly dropped (~20 psi per second for tracking asphaltene onset) to just above the bubble point, and the deposition test begins by setting the flow program to the correct pressure and preferred flow rate. For this testing example, the flow rate is based on currently used pumps and cylinders, but they can be substituted out and not lose functionality of the system allowing for testing in more extreme pressure, temperature, and flow profiles.

Figure 10:
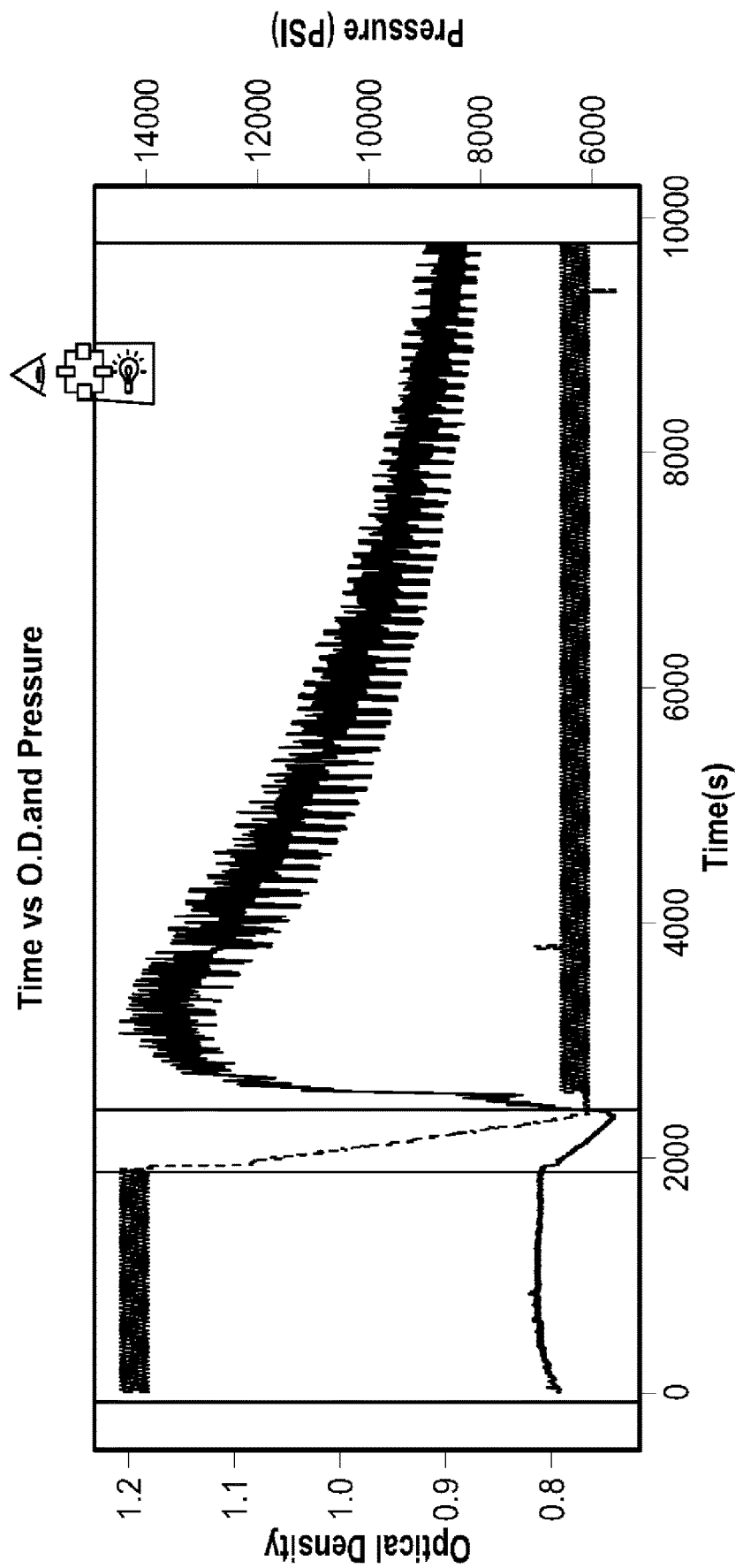
FIG. 10 is an optical density and pressure vs time graph.

For this specific conditions for operating the apparatus, FIG. 10 depicts the pressure profile and optical density at a wavelength of 1600 nm as a function of time during the test (we typically collect 5 different wavelengths during the test but can collect more or less than that depending on which wavelength(s) we are interested in). In the figure, the red region highlights the pressure of the system during a 30-minute mixing phase. This time is necessary to allow the fluid to homogenize after any changes that may have temporarily occurred when the fluid was flashed into the system. The fluid is kept at 14,000 psi while the sample is being pushed back and forth between the pistoned cylinders. When the mixing phase is over, the pressure is slowly dropped at a set rate to the test pressure. The yellow region depicts the slow pressure drop of 20 psi/s. During this time, the fluid is not flowing and only slightly expands as the pressure decreases. Initially the optical density decreases due to the reduction in pressure causing a decrease in the density of the fluid. After the pressure drop completes, the optical density shoots up as the asphaltenes begin to precipitate and darken the color of the fluid. Finally, the green region shows the pressure of the system during the 2-hour test period, where the fluid is transferred back and forth through the deposition tube between the two pistoned cylinders while the asphaltenes are precipitating. During this region, the optical density first increases and then decreases over time. This decrease may be due to deposition, flocculating, or settling as the particles or flocculates grow over time (or some combination of the three).

Figure 11:
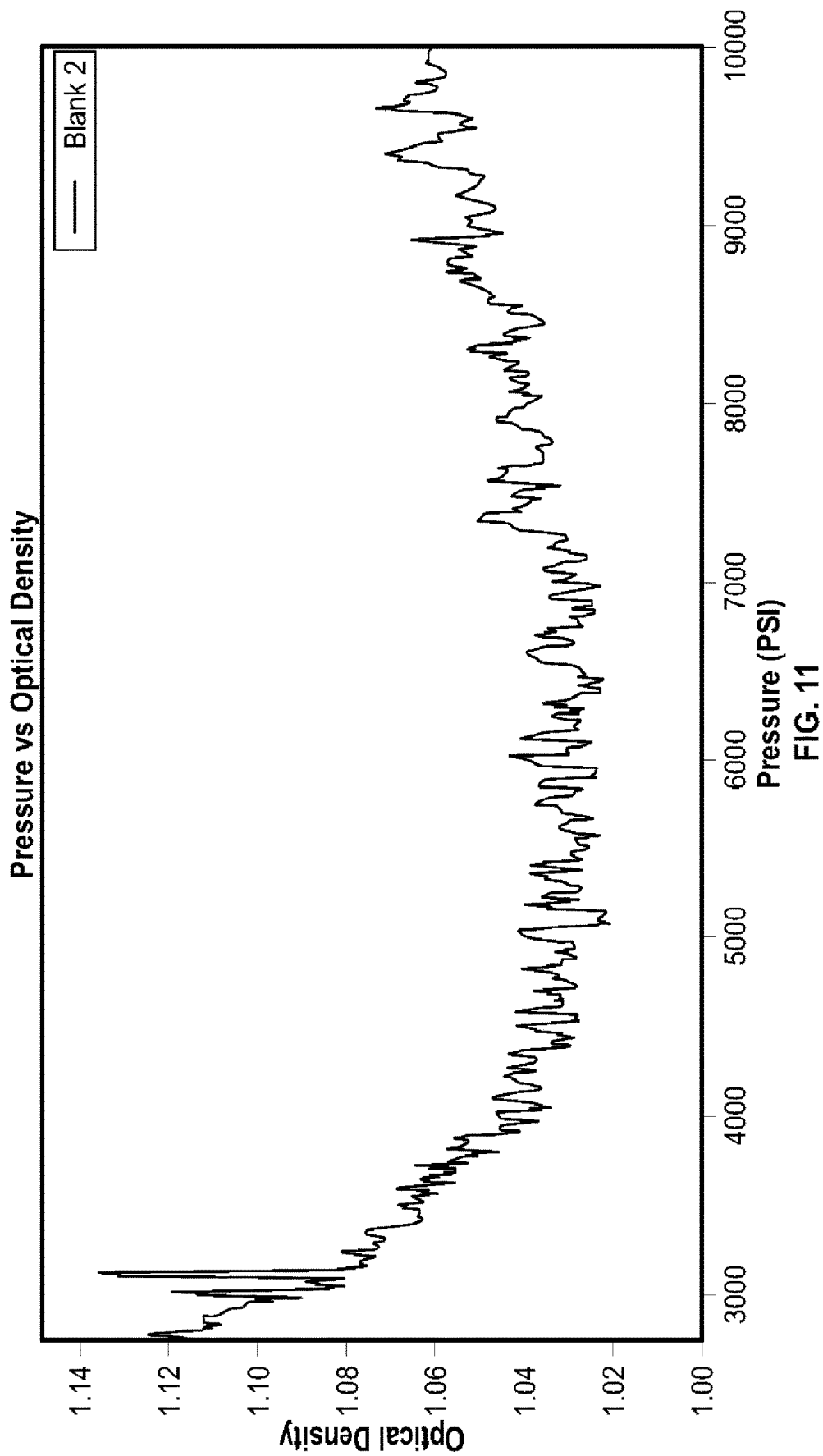
FIG. 11 is an optical density vs pressure graph.

We can determine the asphaltene onset pressure (AoP), by using the optical density and pressure data we collect. FIG. 11 shows the change in OD from 10,000 psi down to 5,000 psi. Once the fluid reaches asphaltene onset pressure—4,200 psi in this case—the OD first levels off as the density change competes with precipitation and then rapidly increases due to increasing flocculation. Actual AoP has to be calculated using a fast and slow depressurization, but an estimate can be obtained from this simplified process.

After two hours, the flow is stopped and valves 101 and 103 are closed off again. The solvent and waste pistoned cylinders are pressurized using high pressure syringe pumps and set to flow from the solvent reactor to the waste pistoned cylinder at 8 ml/min. Valves 102 and 105 are opened and the test fluid is flushed from the system at the test pressure using a non-specific solvent that will remove crude oil from the system while leaving deposited asphaltenes intact. In this iteration, we found a 4:1 mixture of heptane:toluene (by mass) worked very well.

Figure 12:
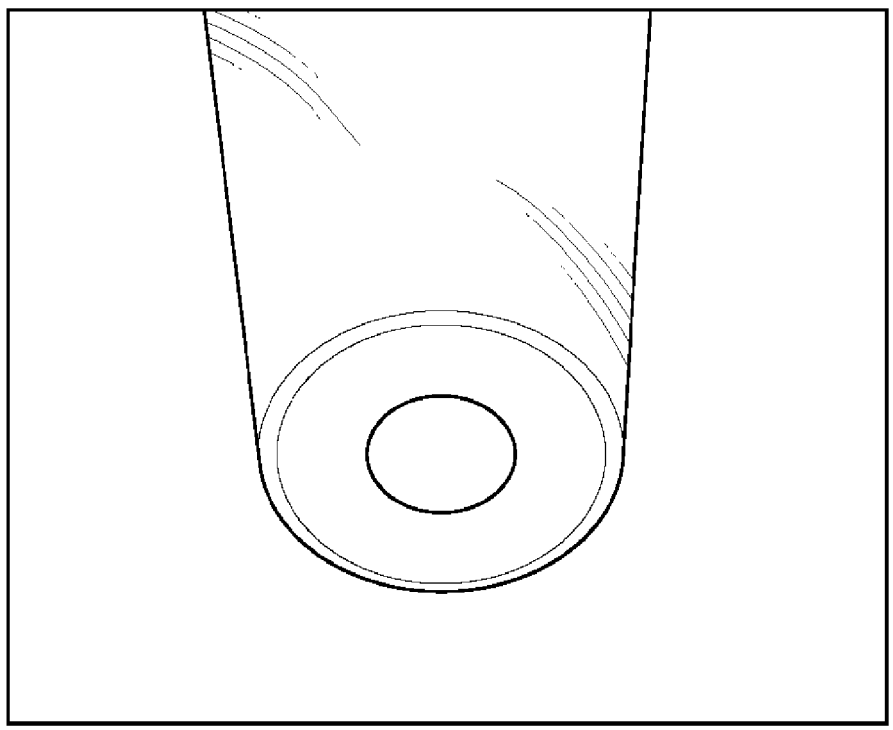
FIG. 12 is a picture of an effluent deposit that has been dried in an oven.

The deposition tube is removed from the system and the top and bottom of the tube are wiped clean of residual materials before attaching clean fittings to rinse the tube. Four mL of rinsing solvent flowing at 2 ml/minute are used to remove any residual crude from the inside of the tube. After the tube has been rinsed, a clean vial is placed below the tubing and 4 mL of a solvent that will completely remove asphaltenes (DCM, chloroform, etc.) at 2 ml/minute is used to extract the asphaltenes that deposited during the test. The solvent used for extraction is then evaporated using nitrogen resulting in the deposit shown in FIG. 12. Two grams of fresh solvent are then added to the vial and the vial is mixed thoroughly.

Figure 13:
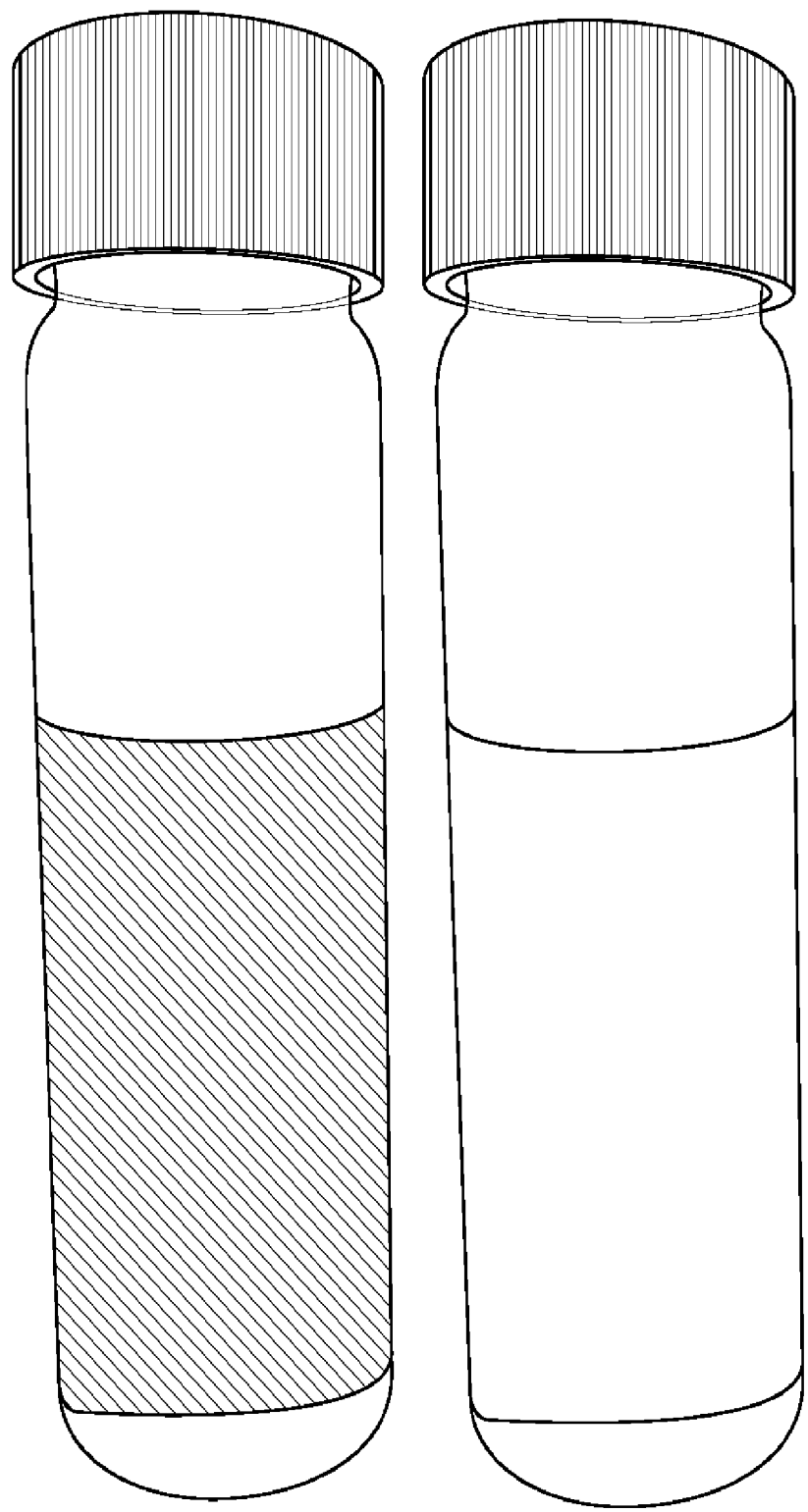
FIG. 13 is a blank and null deposit.
Figure 14:
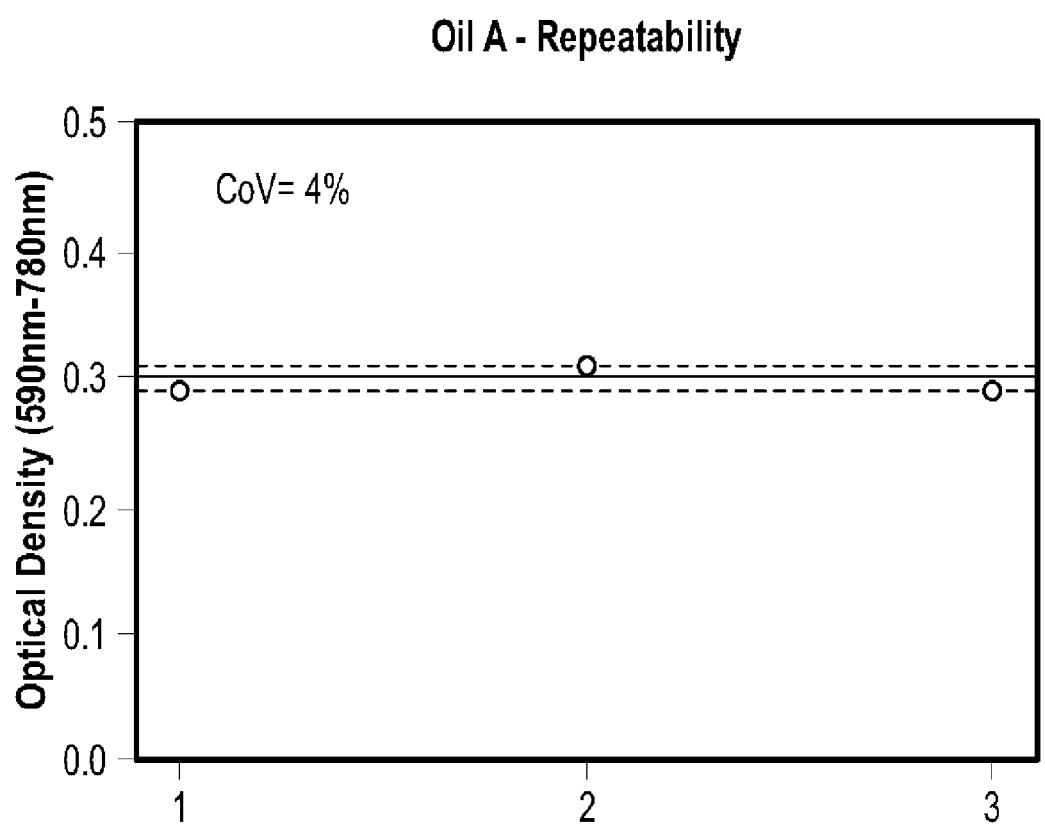
FIG. 14 is a graph of three nearly identical deposits from an untreated South American crude run over three days.

Now the sample is ready for the final analytical measurement. We know that the concentration of the asphaltene species contained in the fluid directly correlates to the absorbance via Beer's law[2] and optical techniques are much more sensitive to detecting asphaltene deposits precisely. So, we take the optical density of the sample at 590 nm and 780 nm within a cuvette having a 10 mm pathlength using a UV/VIS spectrometer. To account for any variation or drift of the spectra, we subtract the 780 nm measurement from the 590 nm and that gives us our final value. A blank standard two-hour run is shown next to a test with a length of 0 hours (no time for deposit to occur) in FIG. 13. The test is very repeatable and the results of three blanks from the same bulk sample run 24 hours apart are shown next to each other and their optical densities are plotted for comparison. The red line in the graph is the average and the standard deviation above and below the average are shown by the green dashed lines in FIG. 14.

Figure 15:
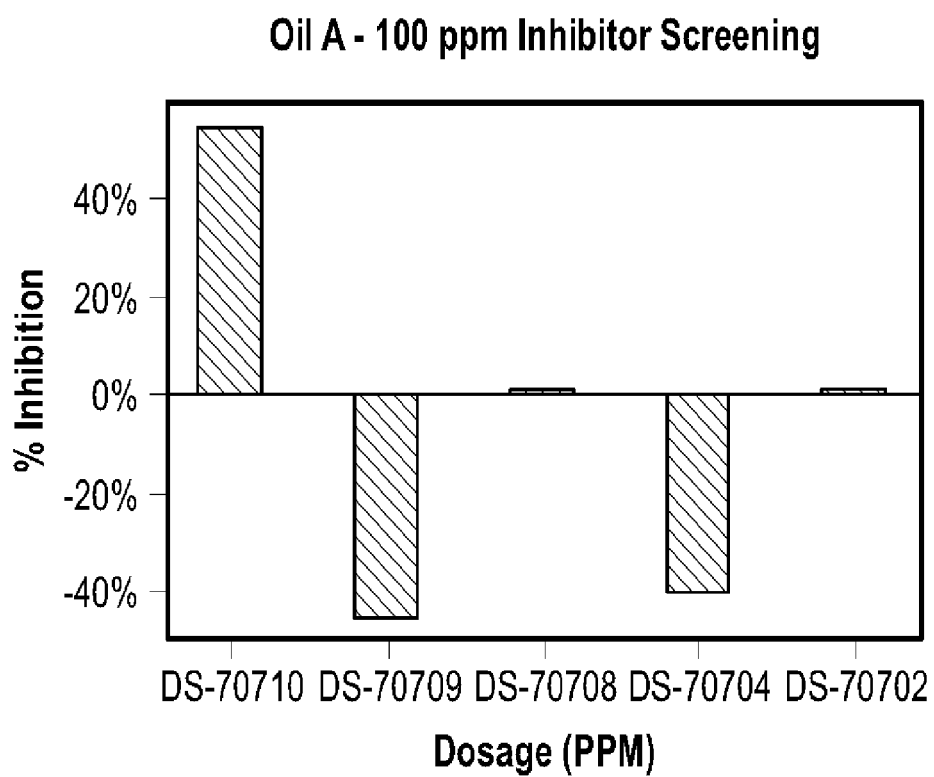
FIG. 15 is a screening of five deepwater qualified products on a South American crude.
Figure 16:
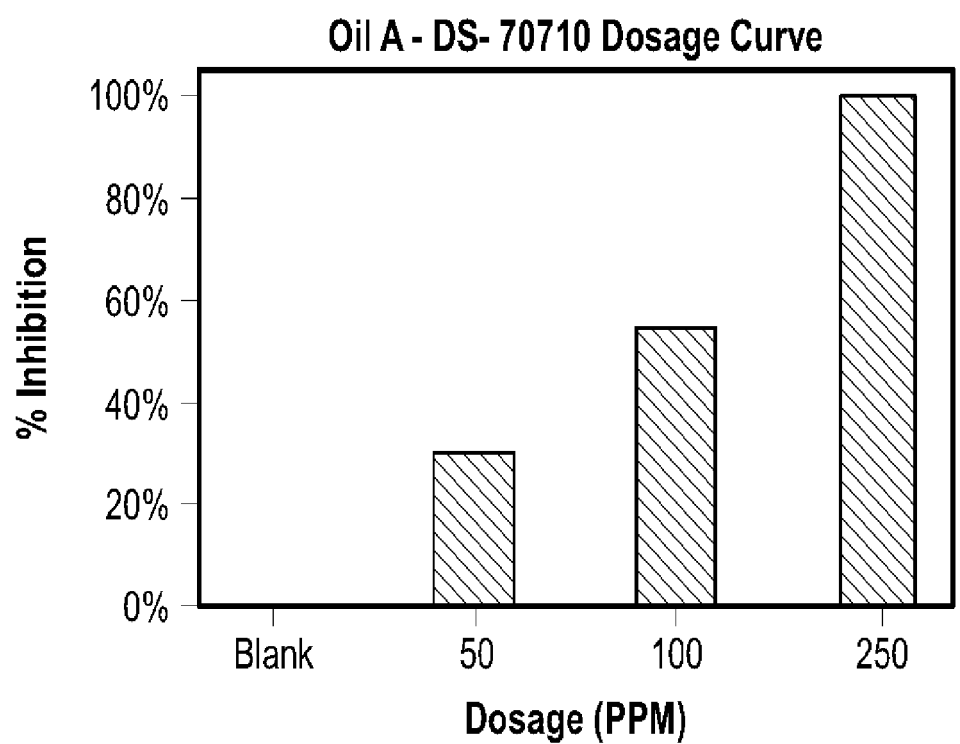
FIG. 16 is a dosage curve for most effective inhibitor showing to fully inhibit deposition during laboratory testing.

A specific example for the utility of this process would be screening inhibitors for performance in a specific crude. We would first perform the test as described above on an untreated crude to obtain a blank value for comparison. We would then inject a predetermined dosage of a select inhibitor into a fresh sample and run the test as usual. An effective inhibitor will prevent deposition and thus have a lighter final color (optical density) measurement than the untreated run, as in FIG. 13. This can be repeated with multiple inhibitors to determine which chemicals are candidates on which to pursue further testing. We have performed this type of testing with this method and some of our results are pictured in FIGS. 15 and 16.

In one example embodiment, a method of determining asphaltene deposition values for a sample of oil, is disclosed. The method may comprise adding an inhibitor to a precision injection tube and bringing an asphaltene sampling system to a specified temperature and pressure. The method may also comprise calibrating a spectrometer when the asphaltene system is in a vacuum state and placing the sample of oil into the asphaltene sampling system. The method may also comprise opening an injection valve in an injection line and filling the injection line of the asphaltene sampling system up to a first cylinder valve and second cylinder valve with the inhibitor and the sample. The method may also comprise opening the first cylinder valve for the first cylinder to fill the first cylinder with a portion of the sample of oil at a desired cylinder flow rate and monitoring the first cylinder to determine a filled condition. The method may also comprise closing the injection valve upon a determination of the filled condition of the first cylinder and opening a second cylinder valve for the second cylinder. The method may also comprise transferring a portion of the sample fluid to transfer into the second cylinder from the first cylinder and closing the second cylinder valve and establishing a pump flow for a first cylinder pump. The method may also comprise closing the injection valve and opening the second cylinder valve, establishing a transfer flow between the first cylinder and the second cylinder of a portion of the sample fluid and dropping a pressure in the system at a desired pressure decrease. The method may also comprise testing at least one of a deposition test and an optical density evaluation of the sample during the dropping of the pressure in the system to determine an asphaltene onset pressure.

In another example embodiment, the method may further comprise cleaning the asphaltene sampling system to remove residual hydrocarbons.

In another example embodiment, the method may be performed wherein the cleaning involves processing one of a solvent and a solvent blend in the system.

In another example embodiment, the method may be performed wherein the calibrating involves obtaining both a light and a dark reference point.

In another example embodiment, the method may be performed wherein the desired cylinder flow rate is between 1 and 30 ml/min.

In another example embodiment, the method may be performed wherein the desired cylinder flow rate is 8 ml/min.

In another example embodiment, the method may further comprise decreasing the pressure in the system to atmospheric pressure; and evacuating the sample from the system.

In another example embodiment, the method may be performed wherein the desired cylinder flow rate is controlled by a high-pressure syringe pump while a bulk storage of the fluid sample is kept at a constant pressure by a separate syringe pump.

In another example embodiment, the method may be performed wherein the transferring of the fluid from the second cylinder to the first cylinder obtains a specific pressure profile for the fluid.

In another example embodiment, the method may be performed wherein the establishing the transfer flow between the first cylinder and the second cylinder of a portion of the sample fluid is maintained by a computer.

In another example embodiment, a system for testing for asphaltene deposition is disclosed. The system may comprise a precision injection tube, an injection valve and an injection line, the injection valve connected to the injection line a first cylinder valve and a second cylinder valve connected to the injection line and a first testing cylinder connected to the first cylinder valve. The system may also comprise a second testing cylinder connected to the second cylinder valve, at least one pump configured to transfer fluid from the first testing cylinder to the second testing cylinder and a spectrometer connected to at least one of the first testing cylinder and the second testing cylinder.

In another example embodiment, the system may further comprise a computer to control a speed of the at least one pump The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. A method of determining asphaltene deposition values for a sample of oil, comprising:
   adding an inhibitor to a precision injection tube;
   bringing an asphaltene sampling system to a specified temperature and pressure;
   calibrating a spectrometer when the asphaltene sampling system is in a vacuum state;
   placing the sample of oil into the asphaltene sampling system;
   opening an injection valve in an injection line and filling the injection line of the asphaltene sampling system up to a first cylinder valve and a second cylinder valve;
   opening the first cylinder valve for a first cylinder to fill the first cylinder with a portion of the sample of oil at a desired cylinder flow rate via a first pump fluidly coupled to the first cylinder;
   monitoring the first cylinder to determine a filled condition;
   closing the injection valve upon a determination of the filled condition of the first cylinder;
   opening the second cylinder valve for a second cylinder;
   transferring a portion of the sample of oil from the first cylinder to the second cylinder and closing the second cylinder valve;
   opening the injection valve and establishing a pump flow for the first pump to refill the first cylinder with a portion of the sample of oil;
   closing the injection valve after refilling the first cylinder and opening the second cylinder valve;
   establishing a transfer flow between the first cylinder and the second cylinder of a portion of the sample of oil;
   dropping a pressure in the system at a desired pressure decrease; and
   testing at least one of a deposition test and an optical density evaluation of the sample of oil during the dropping of the pressure in the asphaltene sampling system to determine an asphaltene onset pressure.

2. The method according to claim 1, further comprising: cleaning the asphaltene sampling system to remove residual hydrocarbons.

3. The method according to claim 1, wherein the cleaning involves processing one of a solvent and a solvent blend in the asphaltene sampling system.

4. The method according to claim 1, wherein the calibrating involves obtaining both a light reference point and a dark reference point.

5. The method according to claim 1, wherein the desired cylinder flow rate is between 1 and 30 ml/min.

6. The method according to claim 1, wherein the desired cylinder flow rate is 8 ml/min.

7. The method according to claim 1, further comprising:
   decreasing the pressure in the asphaltene sampling system to atmospheric pressure; and
   evacuating the sample of oil from the asphaltene sampling system.

8. The method according to claim 1, wherein the first pump is a syringe pump, and wherein the desired cylinder flow rate is controlled by the syringe pump while a bulk storage of the sample of oil is kept at a constant pressure by a second syringe pump.

9. The method according to claim 1, wherein the transferring the portion of the sample of oil from the first cylinder to the second cylinder obtains a specific pressure profile for the sample of oil.

10. The method according to claim 1, wherein the establishing the transfer flow between the first cylinder and the second cylinder of the portion of the sample of oil is maintained by a computer.

* * * * *